United States Patent [19]

Barnes

[11] Patent Number: 5,070,623
[45] Date of Patent: Dec. 10, 1991

[54] PROSTHETIC GAUGE

[75] Inventor: Milton Barnes, Warsaw, Ind.

[73] Assignee: Zimmer, Inc., Warsaw, Ind.

[21] Appl. No.: 521,054

[22] Filed: May 2, 1990

[51] Int. Cl.$^5$ .......................... G01B 3/16; A61B 5/107
[52] U.S. Cl. ........................................ 33/807; 33/512; 33/555.3; 606/102
[58] Field of Search ................ 33/555.1, 555.2, 555.3, 33/783, 807, 808, 511, 512, 797, 806; 606/102

[56] References Cited

U.S. PATENT DOCUMENTS

| | | | |
|---|---|---|---|
| 608,183 | 8/1898 | Davis | 33/797 |
| 1,221,668 | 4/1917 | Brunton | 33/808 |
| 1,251,648 | 1/1918 | Dunn | 33/797 |
| 1,264,571 | 4/1918 | Steinhilper | 33/807 |
| 1,804,064 | 5/1931 | Sison | 33/512 |
| 2,236,443 | 4/1941 | Oboler | 33/555.3 |
| 2,877,559 | 3/1959 | Dahlberg | 33/797 |
| 4,127,112 | 11/1978 | Sherlock et al. | 33/512 |

FOREIGN PATENT DOCUMENTS

| | | | |
|---|---|---|---|
| 0514192 | 3/1921 | France | 33/807 |
| 0821717 | 12/1937 | France | 33/797 |
| 0119874 | 10/1947 | Sweden | 33/807 |
| 0916961 | 3/1982 | U.S.S.R. | 33/555.1 |

Primary Examiner—Thomas B. Will
Attorney, Agent, or Firm—Gene Warzecha

[57] ABSTRACT

A manually operated gauge for the simultaneous measurement of two orthogonal diameters of a spherical member. The gauge comprises four uniquely shaped bars all pivotably connected together about four parallel pivot axes, the bars arranged to enclose a measurement or work space into which the spherical member to be measured may be brought. Two main arms are pivotably joined at one end and each is provided with a pair of orthogonally oriented contact surfaces at the other end, the contact surfaces adapted to arcuately move with their respective arms about the arm-pivot in order to capture a spherical member between them. A scale member is pivotably connected to the free end of one of the arms and an indicator member is pivotably joined to the free end of the other of the arms. The scale member and the indicator member are pivotably connected to each other about an axis aligned along the center line of the gauge while the other ends of the scale member and the indicator member cooperate to indicate the size of the spherical component being measured.

8 Claims, 1 Drawing Sheet

PROSTHETIC GAUGE

BACKGROUND OF THE INVENTION

1. Field of the Invention

The invention relates generally to measurement devices and, in particular, to devices for measuring the dimension of an object such as the diameter of spherical components. Still more particularly, the invention relates to gauges for use in prosthetic applications such as the measurement of the spherical diameter of a femoral head and/or implantable femoral head components.

2. Description of the Prior Art

The use of measurement devices to determine the size of a patient's femoral head is essential in order to enable the use of appropriately sized prosthetic components. For example, during a total hip replacement the size of the patient's femoral head must be determined so that an appropriately sized prosthetic femoral head may be provided on the femoral stem component and also so that the appropriate acetabular cup size is utilized to mate with the implanted femoral head.

It is known in the prior art to use a linear caliper for the measurement of the outside diameter of spherical components such as femoral heads. The same or a similar caliper may be used to measure the inside diameter of the acetabulum. One example of such a caliper is the No. 3895 Townley Femur Caliper available from Zimmer, Inc. of Warsaw, Ind. While useful, this type of caliper can only measure a single dimension at a time and is highly sensitive to the correct placement of the caliper on the femoral head. It should be apparent that the measurement of a spherical dimension with a linear instrument is subject to inconsistent readings unless extreme care is taken in making the measurements. However, even with extreme care, numerous measurements must be made and the caliper must be adjusted for each measurement. Another disadvantage is that the user must often use both hands for proper operation of such calipers.

Other instruments for measuring the diameter of spherical prosthetic heads include open-faced templates and contour gauges provided in a range of discrete sizes so that the surgeon must select the gauge closest in size to the actual head being measured. These are also linear devices subject to the foregoing inaccuracies and also subject to the obvious difficulty of using the gauges when there is a slight mismatch between the available discrete sizes and the actual size of the head being measured. Examples of prior art contour gauges and femoral template sets are also available from Zimmer, Inc.

Some spherical head gauges are available as a set of discretely sized, closed circular openings which are used by matching the head being measured to the circular opening having the best fit. These types of gauges are analogous to the aforementioned contour gauges with the obvious difference that the contour gauge only provides an arcuate portion of a particular circular opening while the circular gauge provides the entire circular opening.

In view of the disadvantages associated with prior art spherical prosthetic gauges, it is an object of this invention to provide a prosthetic gauge for measuring the size of spherical prosthetic components with more facility than available with prior art components.

It is another object of this invention to provide a prosthetic gauge adapted for manual use and capable of providing accurate measurement of orthogonal diameters without being as sensitive to gauge placement on the spherical member being measured as prior art units.

It is a further object of this invention to provide a prosthetic gauge capable of single hand operation.

SUMMARY OF THE INVENTION

These and other objects of the invention are achieved by the preferred embodiment disclosed herein which is a prosthetic gauge capable of measuring two orthogonal diameters of the spherical component being measured. In one embodiment, the invention is an apparatus for measuring the diameter of a spherical member, the apparatus comprising first and second longitudinally extended arms each having a pair of contact surfaces transversely disposed at one end thereof. The contact surfaces of each pair are orthogonally oriented with respect to each other. The other ends of the first and second arms are pivotably joined together. A scale member is pivotably attached to the free end of one of the arms, the scale member being a generally C-shaped structure facing the other arm and having an arcuate scale at one end thereof. An indicator member is pivotably attached to the free end of the other one of the arms, the indicator member being a generally C-shaped structure facing the other arm and having a pointer at one end thereof for cooperating with the arcuate scale to indicate a value. The scale member and the indicator member are pivotably joined to each other to enable movement therebetween in response to relative movement between the arms.

DESCRIPTION OF THE PREFERRED EMBODIMENT

Figure 1:
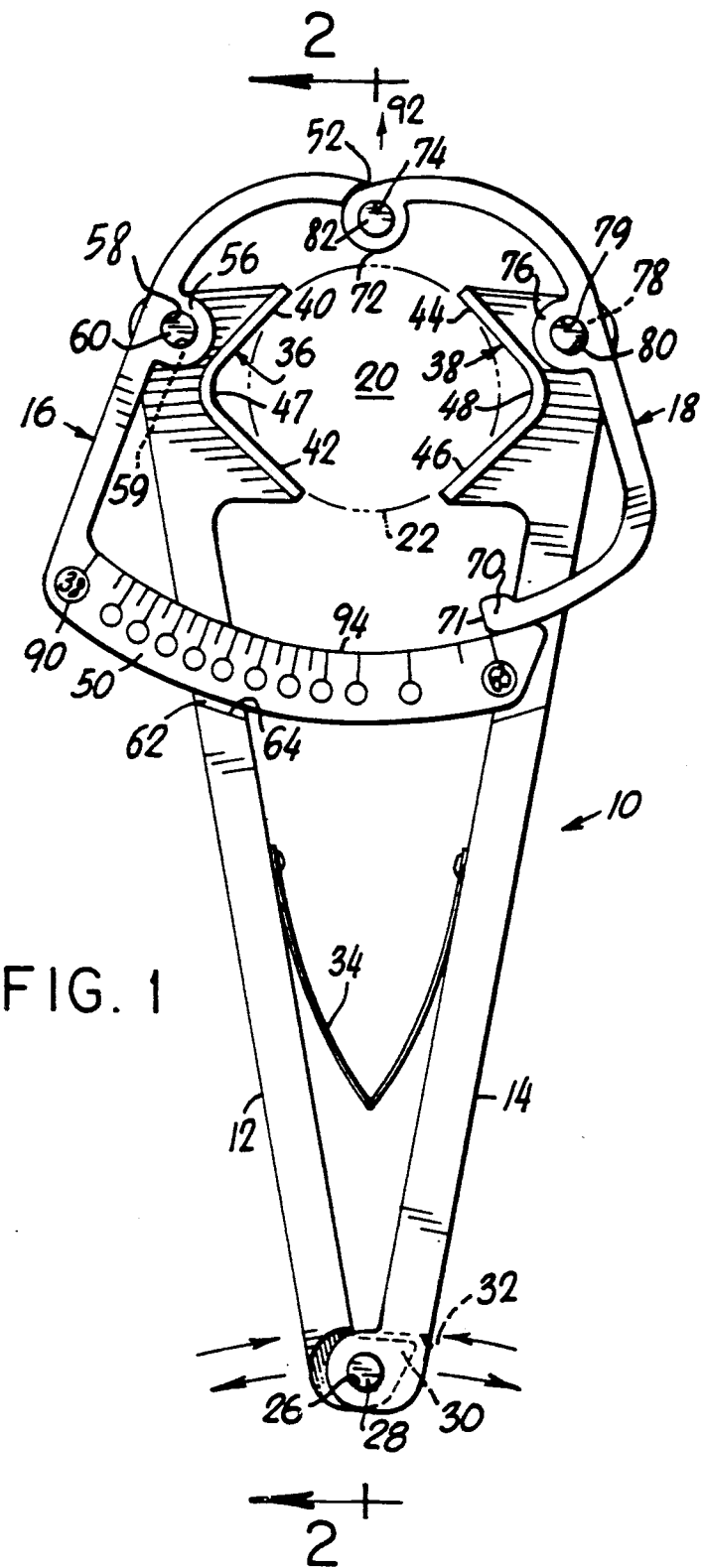
FIG. 1 shows a diagrammatic plan view of a prosthetic gauge constructed in accordance with the principles of this invention.

Referring now to the drawings, it will be noted that prosthetic gauge 10 comprises longitudinally extending arms 12 and 14 as well as a scale member 16 and indicator member 18. As will be understood below, the assembly of these four components is such as to define an enclosed work space 20 into which a spherical member may be placed for measurement. For explanatory purposes a spherical member is shown in phantom at 22.

Longitudinal arms 12 and 14 are provided with apertures 24 and 26, respectively, for receiving a pivot pin 28 secured within the apertures in a conventional manner to enable limited pivotable motion of the arms over a predetermined range. The range of motion of the arms is defined by a cam member 30 integrally formed at the end of arm 12, the cam member intended to abut a ledge 32 integrally formed in arm 14. Conventional spring 34 is positioned to maintain arms 12 and 14 in a normally open condition. The maximum angle opening between arms 12 and 14 being defined by the abutting engagement between cam 30 and ledge 32. As will be understood below, in order to operate the prosthetic gauge, a user need merely position a spherical member in work spaced 20 and squeeze the arms together with one hand.

The free ends of arms 12 and 14 are provided with right angle measurement jaws 36 and 38, respectively. Each jaw is provided with a pair of integrally joined and orthogonally oriented contact surfaces, the orthogonal surfaces associated with jaw 36 and arm 12 being designated 40 and 42 while the orthogonal surfaces associated with jaw 38 and arm 14 being designated as 44 and 46. Each of the contact surfaces may be roughened as shown at 49 in order to enhance the gripping action on a spherical member to be measured. While in the preferred embodiment orthogonal surfaces 40, 42 and 44, 46 are each integrally joined together as right angle members having apex portions 47 and 48, respectively, it will be understood by those skilled in the art that jaws 36 and 38 need not have integrally formed contact surfaces. It is necessary, however, that the contact surfaces of each jaw be spatially fixed relative to each other on their respective arms in order to be oriented tangentially to the surface being measured. As will be understood below, prosthetic gauge 10 measures a spherical member across two orthogonal diameters: one joining opposing surfaces 40 and 46 and the other joining opposing surfaces 42 and 44. In the preferred embodiment, the length of top contact surfaces 40 and 44 is shorter (measured from their respective apices) than the length of bottom contact surfaces 42 and 46. The inner edges of bottom contact surfaces 42 and 46 will meet at the minimum size to prevent any further travel of indicator member 18 in order to prevent it from being jammed into scale member 16.

Figure 2:
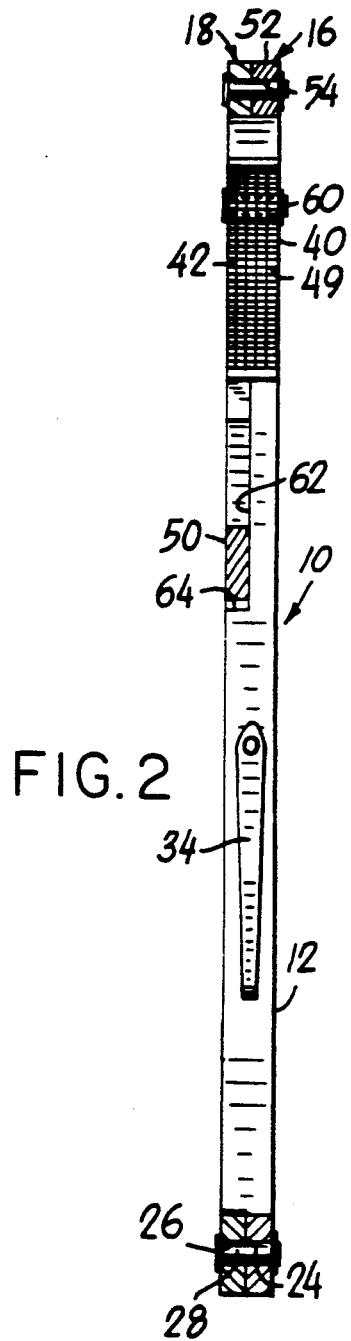
FIG. 2 is a cross-sectional view of FIG. 1 taken along the lines 2—2 thereof.

Scale member 16 is a generally planar, C-shaped structure having an arcuate scale 50 at one end and a boss 52 having an aperture 54 at the other end. Interposed between boss 52 and scale 50 is another boss 56 having an aperture 58. Scale member 16 is pivotably joined via pivot pin 60 to aperture 59 provided at the free end of arm 12. Arm 12 is provided with a cut-away area of decreased thickness at portion 62 having a ledge 64 so that the combined thickness of scale 50 and portion 62 is substantially equal to the thickness of the main body of arm 12 as best seen in FIG. 2. As noted below, this protrusion-free structure produces desirable results.

In a manner analogous to that in which scale member 16 is pivotably joined to arm 12, indicator member 18 is pivotably joined to aperture 78 at the free end of arm 14. Indicator member 18 is a generally planar, C-shaped structure facing working space 20 and provided with a pointer end 70 at one end, boss 72 encircling an aperture 74 at the other end and an intermediate boss 76 having an aperture 79. Pin 80 pivotably secures indicator member 18 to arm 14 while pin 82 pivotably joins the aligned aperture 54 and 74 of bosses 52 and 72.

Scale 50 is provided with a plurality of non-linear indicia 90 (calibrated in 1 mm increments) which cooperate with pointer end 70 to indicate the size of the spherical member being measured. In the preferred embodiment, the scale is read at the spot on the inside arch of the scale at which the end surface 71 of pointer end 70 is aligned. This produces a flat gauge without interferring projections (best seen in FIG. 2) extending out of the plane of the gauge.

It will be understood that the invention produces a significant amplification of the dimension being measured. That is, for the total range of 25 mm that the preferred embodiment can measure, or approximately 1 inch, the indicator travels over a 4 inch scale—a 400% amplification factor. This makes scale 50 considerably easier to read than prior art linear devices where the relationship between the range of actual measured diameters and scale travel is 1:1.

In operation, after a user has placed a spherical member to be measured in work space 20 and squeezed arms 12 and 14 together, contact surfaces 40, 42, 44 and 46 will tangentially engage the spherical member. Simultaneously with the inward motion of arms 12 and 14, pivot pin 82 will by virtue of its being situated at a fixed linear distance relative to pins 60 and 80 move outwardly away from pin 28 in the direction of arrow 92. This motion necessarily causes the radially innermost parts of scale member 16 and indicator member 18 (i.e. pointer end 70 and scale 50) to move toward each other. The radius of curvature of scale 50 is such as to maintain pointer end 70 uniformly spaced from the concave arch surface 94 throughout the entire range of motion of gauge 10.

It will be understood by those skilled in the art that numerous other modifications and improvements may be made to the preferred embodiment of the invention disclosed herein without departing from the spirit and scope thereof.

What is claimed is:

1. An apparatus for measuring the diameter of a spherical member comprising:
a pair of arms pivotably joined at one end at a first pivot axis, the free end of each of said arms adapted to be pivotable about said first pivot axis and provided with a spherical member engaging means for being brought into contiguous engagement with a spherical member to be measured as the free ends of said arms are moved toward each other;
a scale member pivotably joined to one of said arms adjacent said free end thereof at a second pivot axis;
an indicator member for cooperating with said scale member to indicate a measurement made by said apparatus, said indicator member pivotably joined to the free end of the other one of said arms at a third pivot axis;
means for enabling said indicator member and said scale member to move relative to each other as they pivot about their respective axes in response to relative movement between said arms.

2. An apparatus according to claim 1 wherein all said pivot axes are parallel.

3. An apparatus according to claim 1 wherein said spherical member engaging means comprises:
a pair of right-angled, surface members, each member of said pair having a surface parallel to said first pivot axis facing the other and associated with a respective one of said arms and movable therewith to capture a spherical member between said pair of right-angled members when said arms are pivoted about said first pivot axis toward each other.

4. An apparatus according to claim 1 further comprising a spring means operatively interposed between said pair of arms to maintain them in a normally open position.

5. An apparatus according to claim 4 further comprising a stop member associated with said first pivot axis to limit the maximum angle between said pair of arms.

6. An apparatus according to claim 5 wherein said stop member comprises a cam member affixed to one of said arms and a ledge member affixed to the other of said arms to abut said cam member at a predetermined position of said arms.

7. An apparatus for measuring a member comprising:
a first longitudinally extended arm having a first pair of mutually orthogonal contact surfaces transversely disposed at one end thereof;

a second longitudinally extended arm having a second pair of mutually orthogonal contact surfaces transversely disposed at one end thereof;

a pivot means joining said first and second arms at their other ends, said pivot means enabling limited pivoting motion between said arms;

a generally C-shaped scale member pivotably attached at an intermediate point thereof to the free end of one of said arms, said scale member facing the other arm and having an arcuate scale at one end thereof, said scale bearing indicia corresponding to the distances between opposing ones of said first and second pairs of contact surfaces;

a generally C-shaped indicator member pivotably attached at an intermediate point thereof to the free end of the other one of said arms, said indicator member facing the other arm and having a pointer means at one end thereof for cooperating with said arcuate scale to indicate a value representative of a dimension being measured; and means for pivotably joining said scale member and said indicator member to enable movement therebetween in response to relative movement between said arms.

8. An apparatus for measuring a member comprising:

a pair of arms pivotably joined at one end at a first pivot axis, the free end of each of said arms adapted to be pivotable about said first pivot axis and provided with a member engaging means for being brought into contiguous engagement with a member to be measured as the free ends of said arms are moved toward each other;

a scale member pivotably joined to one of said arms adjacent said free end thereof at a second pivot axis;

an indicator member for cooperating with said scale member to indicate a measurement made by said apparatus, said indicator member pivotably joined to the free end of the other one of said arms at a third pivot axis;

means for enabling said indicator member and said scale member to move relative to each other as they pivot about their respective axes in response to relative movement between said arms.

* * * * *